United States Patent [19]

Hope

[11] Patent Number: 4,535,628

[45] Date of Patent: Aug. 20, 1985

[54] APPARATUS FOR LEVEL MEASUREMENTS

[76] Inventor: Bjorn R. Hope, Kampeveien 20, N-1350 Lommedalen, Norway

[21] Appl. No.: 463,885

[22] PCT Filed: May 21, 1982

[86] PCT No.: PCT/NO82/00028

§ 371 Date: Jan. 21, 1983

§ 102(e) Date: Jan. 21, 1983

[87] PCT Pub. No.: WO82/04122

PCT Pub. Date: Nov. 25, 1982

[30] Foreign Application Priority Data

May 22, 1981 [NO] Norway .................................. 811752
May 19, 1982 [NO] Norway .................................. 821682

[51] Int. Cl.³ .................... G01F 23/28; G01N 29/02
[52] U.S. Cl. .................... 73/290 V; 340/621; 367/908
[58] Field of Search ............ 73/290 V; 340/621; 367/908; 318/482; 374/117, 142

[56] References Cited

U.S. PATENT DOCUMENTS

| 3,213,438 | 10/1965 | Felice et al. | 340/244 |
|---|---|---|---|
| 3,326,042 | 6/1967 | Ross et al. | 73/290 |
| 3,456,715 | 7/1969 | Freedman et al. | 340/621 X |
| 3,838,593 | 10/1974 | Thompson | 367/120 X |
| 3,969,941 | 7/1976 | Rapp | 73/321 X |
| 4,123,753 | 10/1978 | Gravert | 340/621 |
| 4,182,177 | 1/1980 | Prough | 73/290 V |
| 4,212,201 | 7/1980 | Hirsch et al. | 73/290 V |
| 4,229,798 | 10/1980 | Rosie et al. | 340/621 X |
| 4,403,508 | 9/1983 | Langlois | 73/290 V |

FOREIGN PATENT DOCUMENTS

| 222586 | 10/1958 | Australia . | |
| 1648997 | 6/1971 | Fed. Rep. of Germany . | |
| 2631037 | 1/1977 | Fed. Rep. of Germany . | |
| 2911216 | 10/1980 | Fed. Rep. of Germany . | |
| 1235054 | 5/1960 | France . | |
| 0356729 | 10/1937 | Italy | 340/621 |
| 141967 | 2/1980 | Norway . | |
| 0829741 | 3/1960 | United Kingdom | 73/290 V |
| 1361052 | 7/1974 | United Kingdom . | |

Primary Examiner—Daniel M. Yasich
Attorney, Agent, or Firm—Frost & Jacobs

[57] ABSTRACT

An apparatus for measuring acoustic transmission characteristics of at least one medium to be measured in which at least one elongated hollow chamber is immersed. The chamber is closed at its bottom end and is filled with an acoustic connecting liquid, and at least two separate movable transducers are immersed in the connecting liquid within the chamber in spaced relation to the wall thereof, the chamber having a cross-sectional shape such that a directional acoustic path between opposite emitter and collector transducers passes through the medium to be measured, the medium being out of direct contact with the transducers.

8 Claims, 16 Drawing Figures

APPARATUS FOR LEVEL MEASUREMENTS

The present invention relates to an apparatus for level measurements of acoustic transmission characteristics of at least one medium to be measured, e.g. for measuring levels of said medium, as stated in the introductory part of the following claims.

From the Norwegian Pat. No. 141 967 an apparatus for level measurements of freely flowing substances, solids or combinations of these in tanks, containers, basins or the like by measuring the acoustic transmission characteristics is known, wherein two separate elongated tubes are arranged, both being closed at their bottom ends, and both tubes being filled with a suitable liquid forming a means of communication between an emitter transducer and a collector transducer which are adjustably provided in their respective tubes. The tubes primarily serve to separate the transducers from the medium to be measured. The transducers are separately connected to a conveyer means for position control and they comprise electrical connections to a signal processing device.

As will appear from said patent the transducers will necessarily have a non-directional radiation pattern, which causes increased power demand, a poor signal/-noise ratio and reduced resolution. The shown solution among others have the constructive disadvantages that synchronous moving of the separate transducers necessitates complicated and relatively expensive equipment and that the general construction of the apparatus in other respects is mechanically complicated and vulnerable.

German Pat. No. 1 648 997 shows a solution, wherein two transducers are secured inside the respective branches of a hollow chamber having a C-shaped cross section. The thickness of the chamber wall is designed to be an integer of $\lambda/2$, $\lambda$ corresponding to the wave length of the utilized transducers. Between each transducer and the wall of the C-shaped chamber there is an insert securing the transducer to the profile wall. A disadvantage of said known solution is among others the necessity of precise operational frequencies for both transducers, and that this requires a complicated installation, especially in chambers of great lengths. Furthermore, every measuring point consists of mutually tuned pairs of transducers which only form one fixed measuring point, so that in case several measuring points are needed this will necessitate a corresponding number of transducer pairs as well as an increased amount of electronics. Also, it is impossible to move the transducer.

The present invention, thus, has the object of providing an apparatus that is less expensive and more simple in production, more reliable in operation, has a high resolution as compared with the known art, and enables control measurements of the function of the apparatus.

The features characterizing the invention will appear from the following claims as well as from the following description with reference to the accompanying drawing.

FIG. 3 shows the apparatus according to the invention mounted on top of a container or the like.

Figure 1:
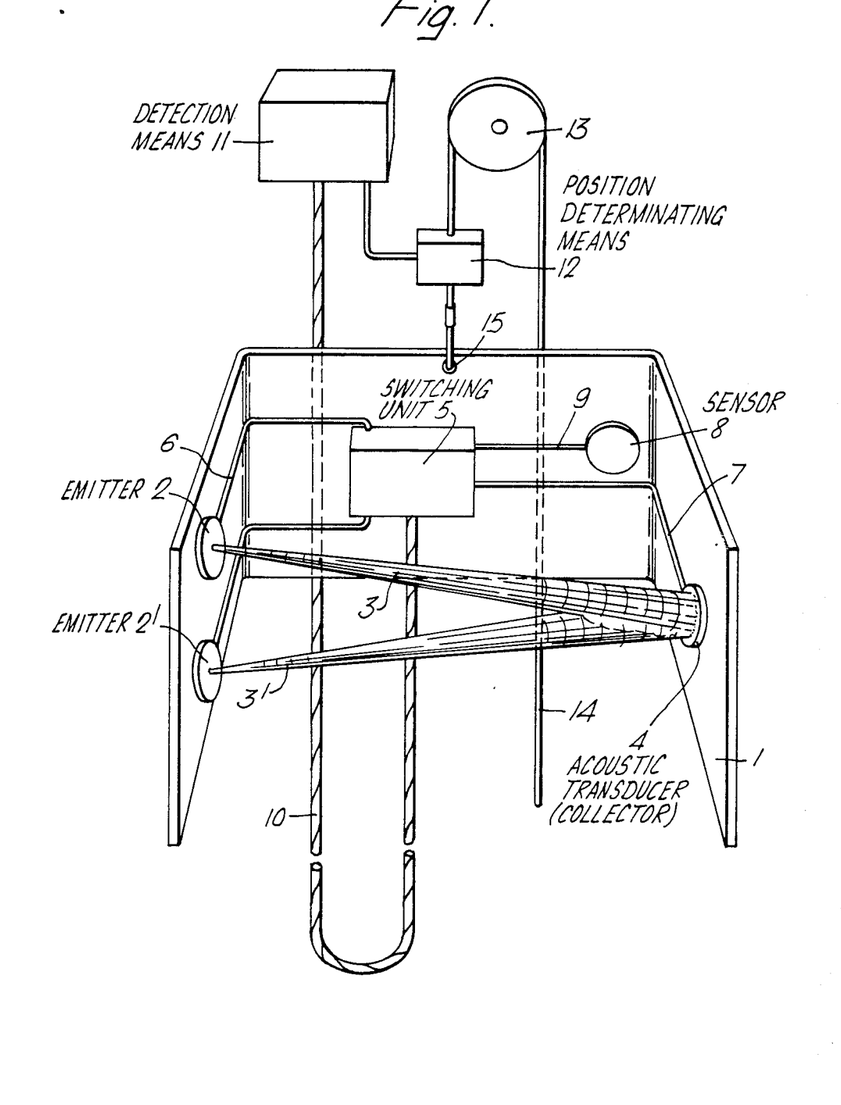
FIG. 1 illustrates the principle of the operation of the apparatus according to the invention.

In FIG. 1 a mounting support 1 is shown connected with a combined control and detection means 11. To one free branch of the mounting support one or several first acoustic transducers (emitters) 2,2' are secured, and at least one second acoustic transducer (collector) 4 is secured to the opposite free branch of said mounting support. A switching unit 5 with optional adapting equipment is connected between said transducers and a signal lead 10. Said transducers are connected with said switching unit via leads 6 and 7 resp. For registration of temperature at the same position it may, furthermore, be suitable to provide a temperature sensor 8 on the same mounting support 1. Said sensor 8 is connected to switching unit 5 via lead 9. Means 11 may be a micro processor with associated suitable control and signal means. The mounting support 1 is displaceable e.g. by a wire 14 connected to a suitable point 15 on said support. Wire 14 is arranged over a pulley 13 for displacement of mounting support 5 in the longitudinal direction of a chamber. Wire 14 can be guided by a vertical position determinating means 12 in the shown embodiment.

When directed acoustic waves are transmitted from emitters 2 and 2' resp. said waves will be received by collector 4 rather in the shape of rays 3,3'. If the transition zone is present between emitters 2 and 2' collector 4 will receive said wave signals 3, 3' with a different character (e.g. as regards phase, amplitude, time), which may form the signal basis for controlling the vertical position of the mounting support when the apparatus is to follow the change of level of the transition zone. In this manner it is, thus possible to detect an interface effectively with high resolution and to let the mounting support follow said interface if desired.

Mounting support 1 is constructed always to provide the transducers in fixed mutual positions and to have the acoustic path fixed in one direction, the position of the support in the chamber simultaneously bringing about the most advantageous acoustic path in relation to the chamber and the medium to be measured.

The secondary acoustic signal path that will arise between the transducers via the mounting support itself and possibly the chamber, may be utilized as a control function of the fact that the system performs satisfactorily, especially in those cases where the medium to be measured has no or low acoustic transmission of the primary signal.

Figure 2:
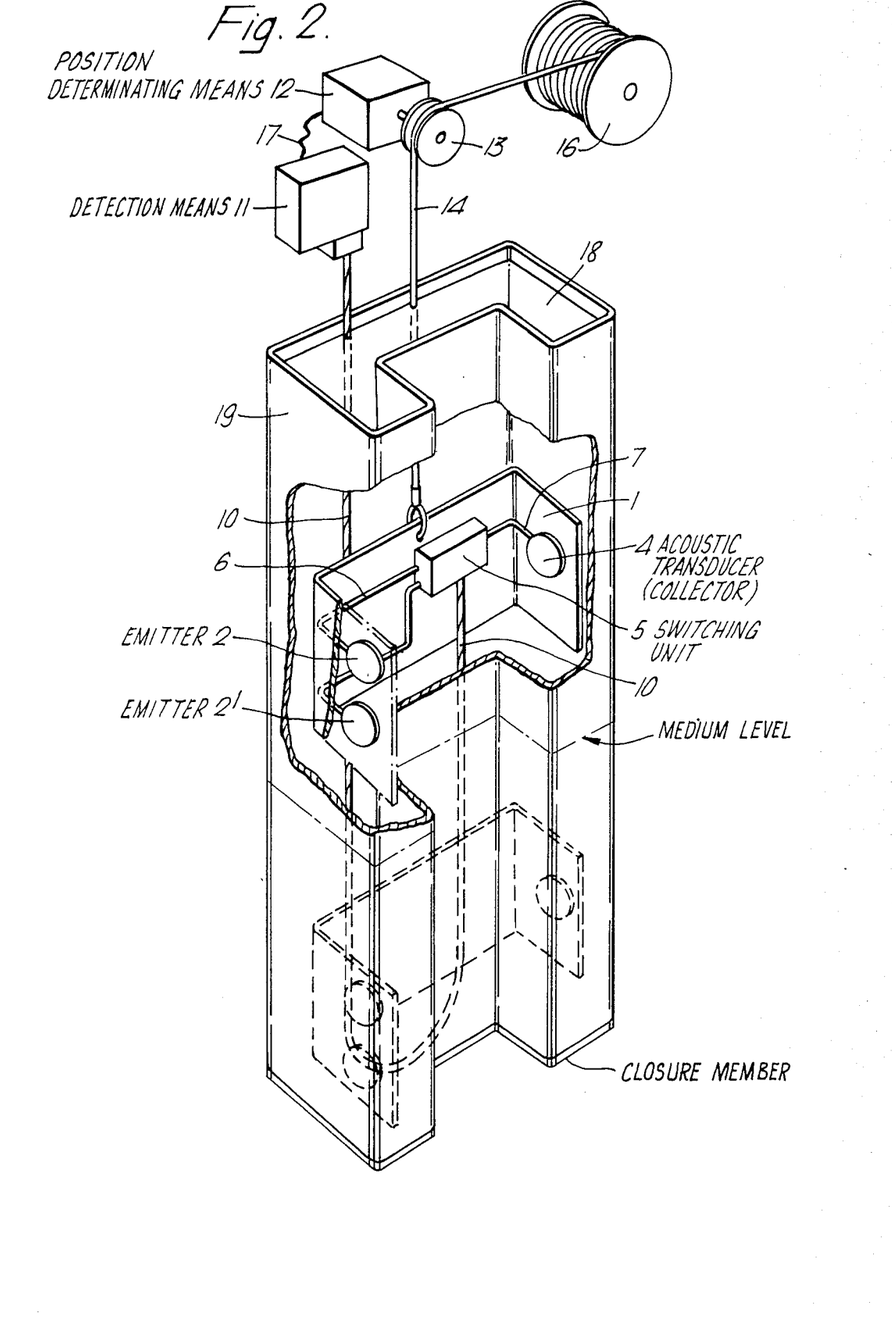
FIG. 2 shows the apparatus according to the invention provided in a hollow chamber.

In FIG. 2 the mounting support 1 with said transducers and switching unit is shown mounted in one single guiding chamber 19, the bottom of which is closed. Chamber 19 is filled with an acoustic connecting liquid 18 which is preferably electrically insulating. In the apparatus shown in FIG. 2 wire 14 passes over pulley 13 from a reel 16 and the position of the support is recorded by means 12 via the wire and the pulley 13. Means 12 communicates with control and recording means 11.

Mounting support 1 may be moved by the aid of an electric, hydraulic, or pneumatic drive, e.g. a step motor. Alternatively movement may be provided by replacing wire 14 e.g. by a metal ribbon, e.g. provided with perforations for engagement with a so called quide wheel. A further alternative manner of moving said support is to connect its upper portion with a buoyancy body, so that said support can be moved along said chamber in a controlled manner by the aid of variations of the connecting liquid level in said chamber.

Figure 3:
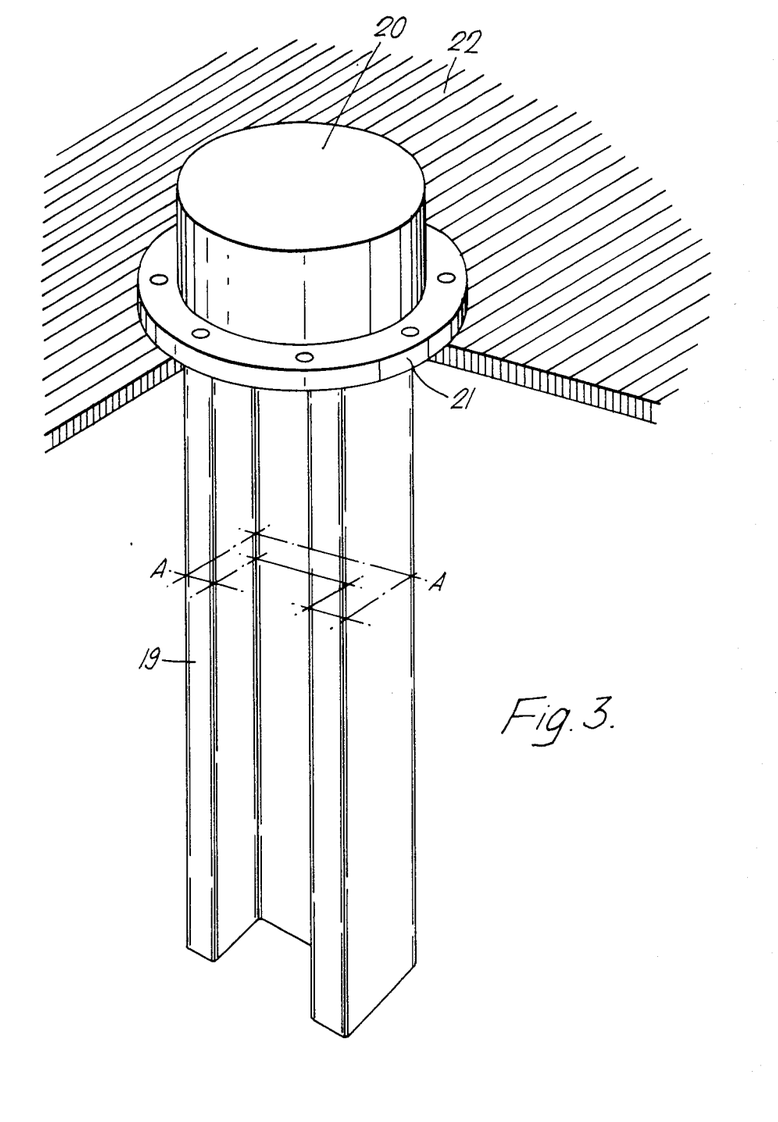

In FIG. 3 the apparatus according to the invention is encased with a top cover comprising a hat 20 and a securing flange 21. The securing flange may be screwed or welded onto a container top 22.

Figure 4:
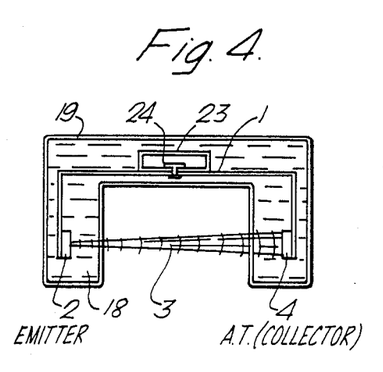
FIG. 4 illustrates a cross-section taken along the line A—A in FIG. 3.
Figure 5:
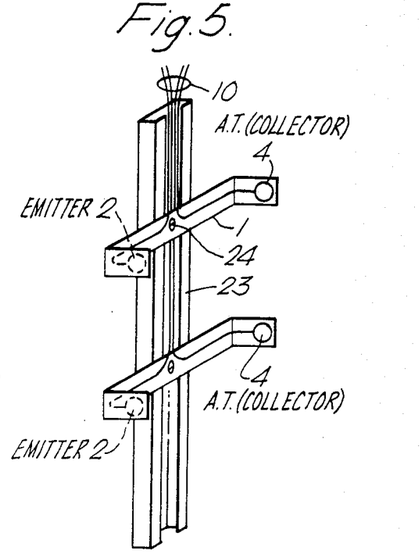
FIG. 5 illustrates the arrangement of the transducers in the apparatus according to FIG. 3.

In FIGS. 4 and 5 several groups of mounting supports are shown on a common securing means 23. The respective supports can be separately and infinitely variably moved along securing means 23 and be secured to said means, e.g. by a screw joint 24 to the desired position. Means 23 with supports can be inserted freely into chamber 19 from above without any necessity of releasing said chamber with its associated flange from the tank. In this manner installation, maintenance and adjustment of all kinds may be carried out with the tank being hermetically closed to the atmosphere to avoid any explosion hazard when the medium to be measured is of an explosive kind.

Figure 6:
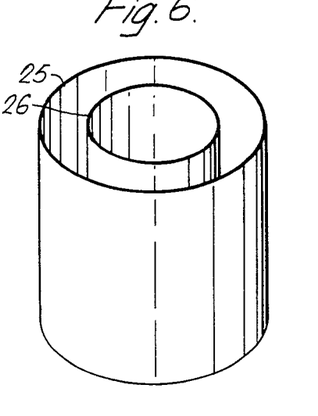
FIGS. 6-11 illustrate various kinds of hollow chambers of an apparatus as shown in FIG. 1.
Figure 7:
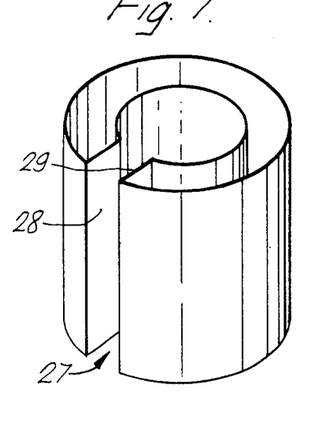
Figure 8:
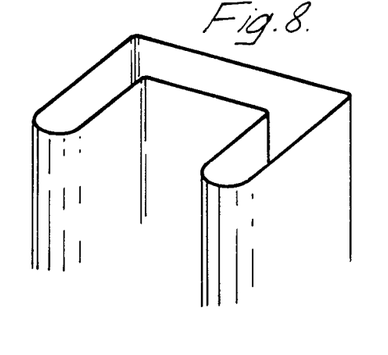
Figure 9:
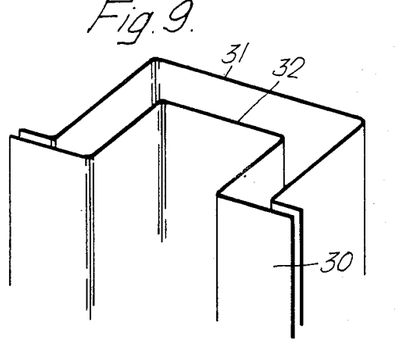
Figure 10:
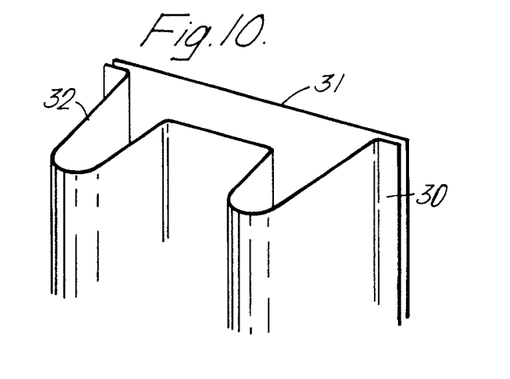
Figure 11:
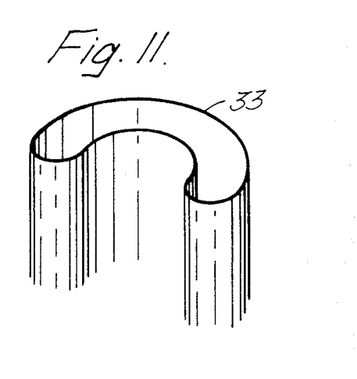

In FIGS. 6–11 various embodiments of profile 19 are shown. As shown in FIG. 2, geometrically shaped chamber 19 may have a generally U-shaped cross section, as indicated in FIGS. 8–11 as well. In FIG. 6 the chamber comprises an outside tube portion 25 and an inside tube portion 26, which gives the chamber a generally O-shaped cross section. The medium to be measured is then to be found within tube portion 26, whereas a suitably designed mounting support and the connecting liquid are arranged between tube portions 26 and 25. In FIG. 7 a slot 27 is shown in the chamber shape of FIG. 6, which gives the chamber a generally C-shaped or key hole shaped cross section. The primary acoustic path here will be between walls 28 and 29, said walls being parallel. As indicated in FIG. 9 as well as 10, the chamber may be constructed of welded parts, e.g. parts 31 and 32, welding flanges 30 being formed in the welding process. In FIG. 11 the chamber 33 has an approximate U- or C-shape, said chamber e.g. being formed by rolling a tube which has a generally circular cross section originally. The chambers shown in FIGS. 6, 7, and 11 may be extruded chambers. A chamber shape like that of FIGS. 9 and 10 may naturally also be achieved by extrusion, in which case flanges 30 are omitted.

The control and recording means 11 comprises means for controlling the movements of mounting support 1 in at least one of the following operational modi: (a) selective setting on a firm position in the guiding chamber 19, (b) accompanying the movement of one or several interfaces in the medium to be measured, and (c) scanning along the entire length of the guiding chamber for recording the acoustic transmission characteristics of the medium to be measured along the length of the guiding chamber.

With the present invention an apparatus is, thus, provided which with its single guiding chamber shows great mechanical strength, is less expensive and simpler in production, has low power consumption due to high directivity and high intrinsic safety, especially in explosive surroundings. Due to the fact that the transducers are connected with a common support, movement of said transducers is possible in an easily controllable manner. To ensure a smoothest possible movement of said support in the guiding chamber, said support may comprise means, e.g. springs or rollers which form a light contact with the interior wall of the guiding chamber.

Figure 12:
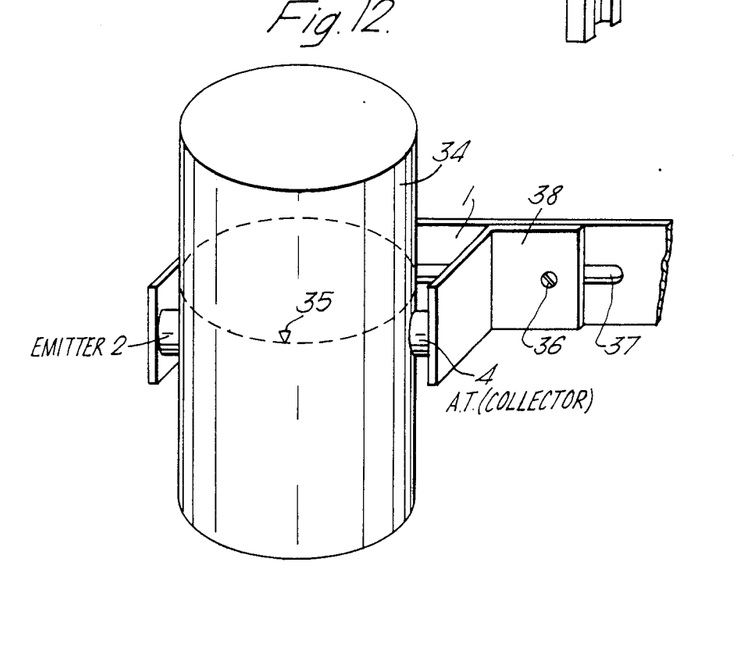
FIG. 12 shows a modification of the apparatus according to the invention, designed for measurement of media to be measured provided in a closed container.

In FIG. 12 emitter 2 and collector 4 are mounted on a common support 1 which is adjustable by the aid of a screw 36, a groove 37 and a bracket 38. The transducers 2 and 4 are made to form a food acoustic contact with the container 34 containing the medium to be measured. In this manner e.g. the levei 35 of the medium in container 34 may be measured without said transducers having direct contact with the medium to be measured. Transducers 2 and 4 are only in contact with container 34, the outside wall of it serving as a guiding chamber for the transducers.

Figure 13:
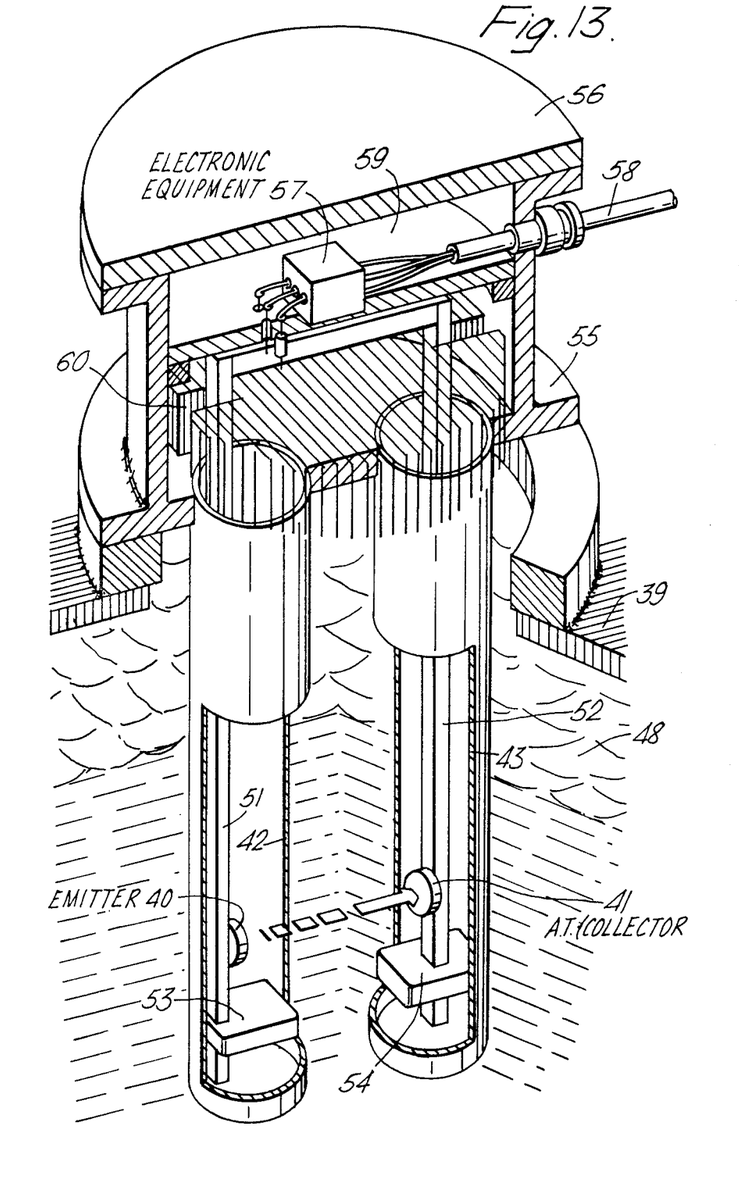
FIG. 13 shows a modification of the level meter according to FIGS. 3-5, especially for use as a high level alarm device, partly shown in section.

FIG. 13 shows a modification of the level meter of FIGS. 3 to 5, this embodiment being designed as a high level alarm that is triggered when the level reaches one or several fixed levels in a container 39 (tank). This meter is also partly based on the technology appearing from the same principle as Norwegian Pat. No. 141 967.

In the present embodiment emitter 40 and receiver 41 transducers are firmly mounted in separate tubes 42 and 43 resp. The tubes surrounding the transducers are filled with a suitable connecting liquid and are closed at their bottoms.

Figure 14A:
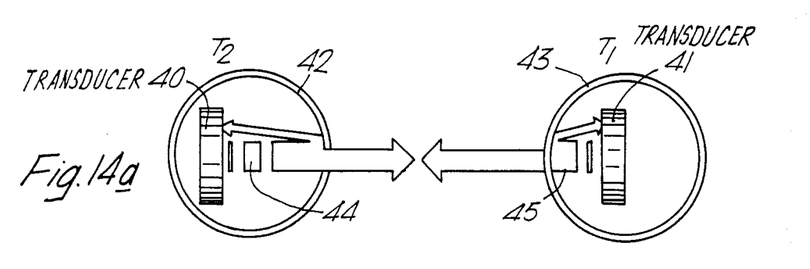
FIGS. 14a and 14b illustrate the principle of the embodiment according to FIG. 13.
Figure 14B:
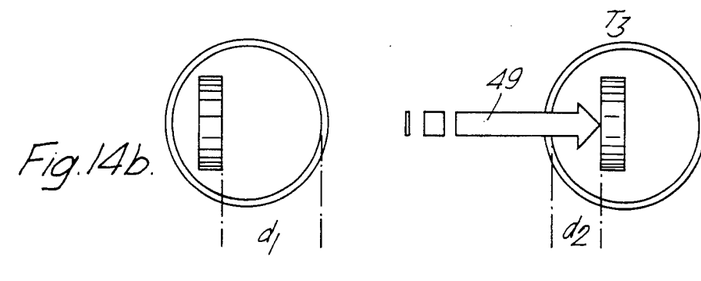

A requirement of a high level alarm having an alarm function is that its functioning must be possible to test in a dry state as well, In the present case this problem is solved by a manual or automatic function which means that both transducers 40, 41 serve as emitter and receiver in a test function. Each transducer sends an acoustic wave 44; 45 towards the inside of the respective tube wall 42; 43 and said wave is reflected back to the transducer 40; 41, which transforms it to an electrical signal at times $T_1$ and $T_2$ regarding transducer 41 and 40 respectively.

Due to the fact that the transducers are mounted at a different distance $d_1$ and $d_2$ resp. from the tube wall, as seen in the transmission direction, this time difference will be somewhat variable for the respective transducers.

Figure 15:
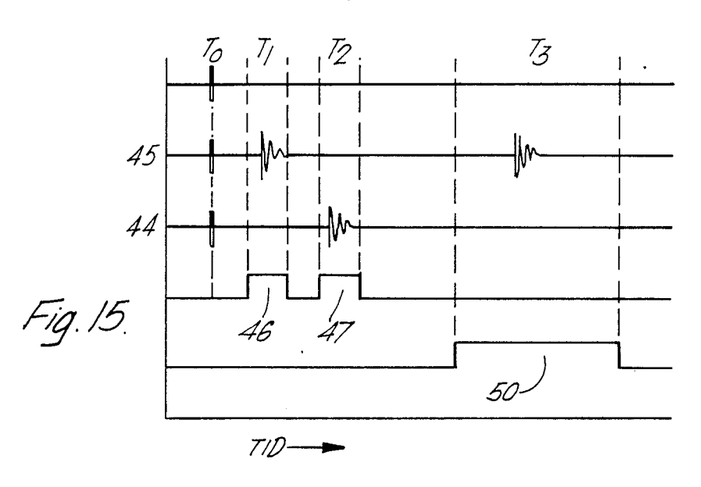
FIG. 15 is a time diagram for a closer illustration of the operation of the level meter according to FIGS. 13 and 14.

A precision timer circuit (not shown) controls the sequence of emission of the respective transducers. The times of the emitted signal and the received signal are compared synchronously. In the test function the time interval between the emitted signal and the received signal from both transducers will be relatively short, but with a small relative difference in time (short pass time between transducer and tube wall being mutually somewhat different).

When both received signals are within a time window 46 and 47 resp., (FIG. 15) the test is accepted and is simultaneously a confirmation of the fact that each transducer 40, 41 functions both as an emitter and as a receiver.

If there is a medium to be measured present as indicated at 48 in FIG. 13, between the tubes level with the positions of the transducers, an acoustic signal 49 will additionally be received at time $T_3$ as a consequence of the fact that a large portion of the acoustic signal passes through tube wall 42 and the medium between tubes and that the sound wave 49 penetrates the tube wall 43 on the receiving side and is there transformed to an electrical signal which differs in time from that of the test function because of a far longer pass time, and which will appear within a certain time window 50. Signals appearing within said time window are a measure of the fact that an acoustically conductive medium level covers the meter at transducer level.

Even though only two transducers are shown in the chosen embodiment, it will be obvious that two or more transducers may be arranged in each tube, dependent on the number of levels to be measured.

As appears from FIG. 13, transducers 40, 41 are mounted on respective rails or the like 51, 52. Undermost said rails may comprise a fixing block 53 and 54 resp., which preferably has a rectangular shape. Like the solutions described above, the present embodiment may be made gas tight, the tubes ending in a collar 55 on top, the exterior portion of which is extended upwards by a cylindrical wall, on which a cover 56 may be secured. Inside said cylindrical portion an intermediate cover 59 may advantageously be provided, on which e.g. electronic equipment 57, leads 58 or the like may be arranged with ducts to the transducers. Said rails should be kept in place by a fixing block 60.

I claim:

1. An apparatus for measuring acoustic transmission characteristics of at least one medium to be measured, e.g. for measuring levels of the medium, in which at least one elongated hollow chamber is immersed, said hollow chamber comprising a guiding chamber filled with an acoustic connection liquid, wherein at least two separated transducers are immersed in said connection liquid inside said guiding chamber, said transducers being arranged on respective branches of a mounting support so that said transducers face one another said guiding chamber having a cross-sectional shape such that a directional acoustic path between opposite transducers passes through said medium to be measured, said guiding chamber being closed at its bottom to avoid contact between said medium and said transducers, and wherein said mounting support on which said transducers are mounted has a cross-sectional shape substantially the same as that of said guiding chamber, but of a lesser cross-sectional area than that of said guiding chamber, one said transducer being arranged on one side of said support and serving as an emitter of an acoustic wave that is emitted toward another said transducer serving as a collector on the other side of said support, said support being selectively movable within said chamber, the primary acoustic path extending from said emitter, through said connection liquid surrounding it, through the wall of the guiding chamber adjacent thereto, through the medium to be measured, through the guiding chamber wall near the collector, through the connection liquid surrounding said collector and to the collector itself.

2. An apparatus as claimed in claim 1, wherein a directional acoustic path from said emitter to said collector forms an angle with the horizontal.

3. An apparatus as claimed in claim 1 or 2, wherein a secondary acoustic path extends from said emitter to said collector via the body of the mounting support.

4. An apparatus as claimed in claim 3, wherein said secondary acoustic path extends from said emitter to said collector via said chamber for forming a reference and test signal path.

5. An apparatus as claimed in claim 1 or 2, wherein a a temperature sensor is mounted on said support, the total effect of the transmission characteristics being obtained by recording a temperature profile and an acoustic connection at the same level.

6. An apparatus as stated in claim 1 or 5 characterized in that said transducers (2,4,8) are connected via a coupling link (5) to a contol and recording means (11), which means comprises members to control the movement of said mounting support in at least one of the following operational modi:
   (a) a selective setting on a fixed position in said profile,
   (b) accompanying the movements of one or several interfaces in the medium to be measured, and
   (c) tracing along the entire length of said profile.

7. An apparatus as stated in claim 1, characterized in that said guiding chamber has a O-, C-, U-, V-, or key hole shaped cross section.

8. An apparatus for measuring acoustic transmission characteristics of at least one medium to be measured, and for testing operability comprising two elongated separate spaced chambers immersed in said medium, each chamber being a hollow tube closed at its bottom end and filled with an acoustic connection liquid; at least one transducer in each hollow tube, each said transducer serving as an emitter and a receiver of sonic pulses, said transducers being mounted stationary in their respective hollow tubes and facing each other in such manner that respective distances between each transducer and an adjacent inside wall of its tube are different; and a rail in each said tube to which each transducer is attached stationarily, said rail at its lower portion being provided with a fixing block which forms a contact with the inside closed bottom end of each said tube; wherein for each sonic signal test function each transducer serves as both an emitter and a receiver and is caused to emit a sonic pulse and thereafter to receive a reflected part of the respective sonic pulse from said adjacent inside wall of its tube; and wherein for testing in a dry state or when medium to be measured is present between said tubes, when said medium to be measured is present between said tubes, the arrival of the received and said reflected parts of the sonic pulses being received within respective time window portions of the sonic pulses to serve as a confirmation test that each said transducer functions as both the emitter and receiver.

* * * * *